United States Patent [19]

Björk et al.

[11] Patent Number: 4,655,595

[45] Date of Patent: Apr. 7, 1987

[54] ELLIPSOMETRIC METHOD AND APPARATUS FOR STUDYING PHYSICAL PROPERTIES OF THE SURFACE OF A TESTPIECE

[75] Inventors: Nils A. N. Björk, Täby; Erland T. Sandström, Mölndal; Johan E. Stenberg; Lars B. Stiblert, both of Gothenburg, all of Sweden

[73] Assignee: SAGAX Instrument AB, Täby, Sweden

[21] Appl. No.: 777,646

[22] Filed: Sep. 19, 1985

[30] Foreign Application Priority Data

Sep. 20, 1984 [DE] Fed. Rep. of Germany ....... 3434575

[51] Int. Cl.$^4$ .......................... G01N 21/21; G01J 4/00
[52] U.S. Cl. .................................... 356/369; 350/394
[58] Field of Search ................ 250/225; 356/364–365, 356/369, 445, 448; 350/394, 395, 396, 397

[56] References Cited

U.S. PATENT DOCUMENTS 4,332,476  6/1982  Stenberg et al. .................... 356/369

FOREIGN PATENT DOCUMENTS 0019088  3/1984  European Pat. Off. ............ 356/369

Primary Examiner—Eugene R. LaRoche
Assistant Examiner—Steven J. Mottola
Attorney, Agent, or Firm—Fleit, Jacobson, Cohn & Price

[57] ABSTRACT

In an ellipsometric method and apparatus which, in order to increase the degree of measuring accuracy, uses the principle of comparative ellipsometry in measuring a characteristic such as a layer thickness, a reference surface is divided into first and second equal surface portions with respectively different reflection characteristics which are in substantially symmetrical relationship to the reflection characteristics of the testpiece, the surface portions preferably comprising two different tapering surface layers extending in parallel relationship to each other.

22 Claims, 8 Drawing Figures

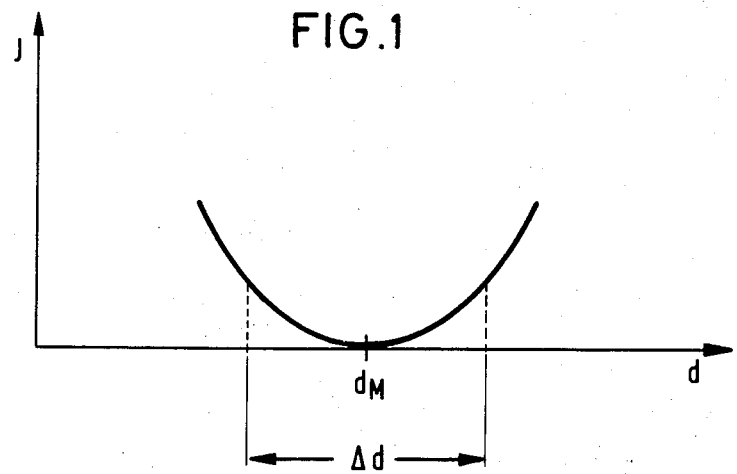
FIG. 1
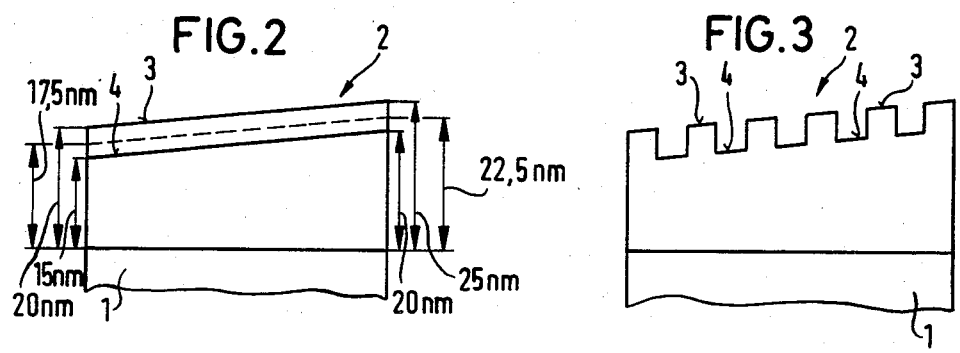
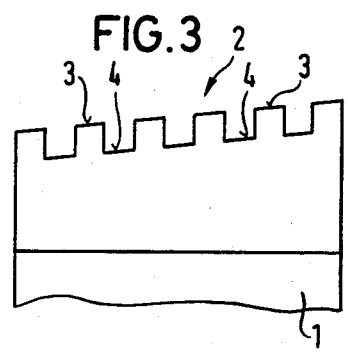
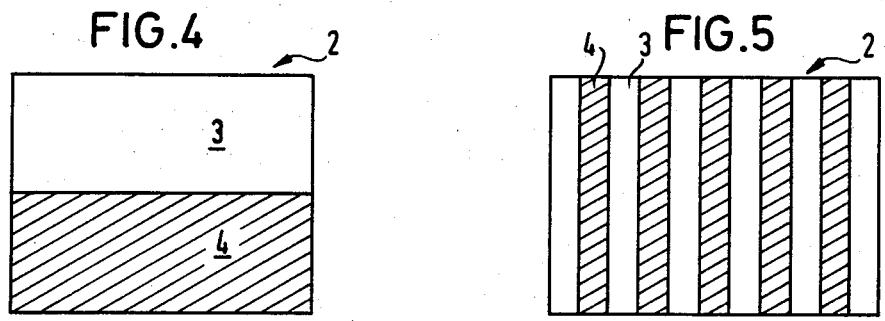
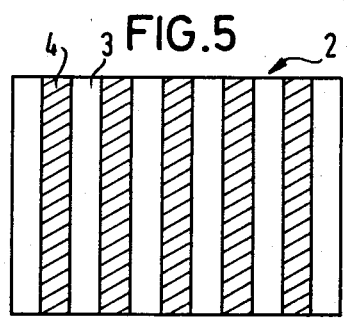
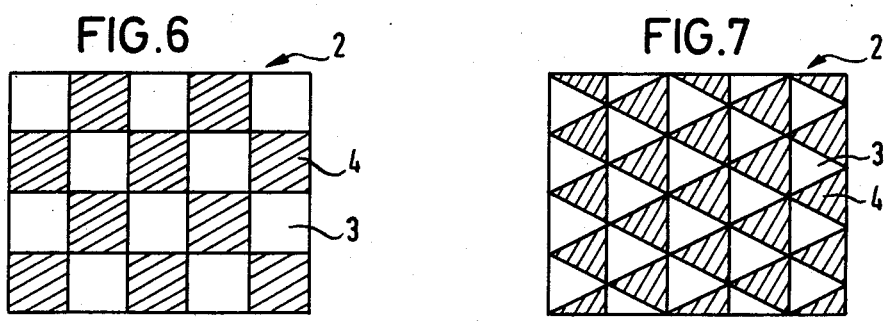
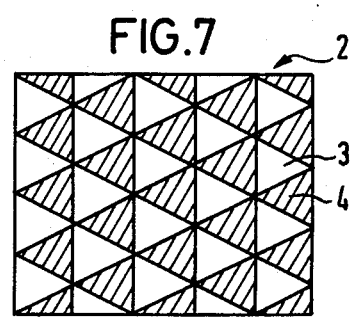

ELLIPSOMETRIC METHOD AND APPARATUS FOR STUDYING PHYSICAL PROPERTIES OF THE SURFACE OF A TESTPIECE

BACKGROUND OF THE INVENTION

The invention relates to an ellipsometric apparatus.

An ellipsometric apparatus is disclosed in European patent specification No. 19088. That comparative ellipsometer makes it possible to investigate physical surface properties, for example the thicknesses of layers or films on the surfaces of testpieces or samples, in an eyepiece, directly and without the assistance of expensive electronic evaluation equipment. For that purpose, light which is polarised by a polariser is caused to be reflected at a reference surface with known reflection characteristics, and a surface of a testpiece which is to be investigated, with the angles of incidence at each surface being the same, the reference surface and the testpiece surface being perpendicular to each other with their angles of incidence or the direction of polarisation of the radiation being turned through 90° between the two surfaces in question. If the reflection characteristics of the reference surface and the testpiece surface are the same, for example if a layer or film which is to be found on the surface of the testpiece is of the same thickness as a layer or film on the reference surface, the light is extinguished by an analyser disposed downstream of the testpiece. When using a reference surface having a layer thereon which is of a wedge-like or tapered configuration, together with an associated suitable reading-off scale, the procedure is that, when the thickness of the layer or film on the surface of the testpiece is found to be the same as a given location on the tapered layer on the reference surface, a dark measuring strip can be seen at a given location on the scale, in the eyepiece which is disposed downstream of the analyser. In that way it is possible to measure layer thicknesses of from 2 nm up to 50 μm, with a high degree of accuracy which in many cases may be better than ±2%.

In the apparatuses which have been disclosed hitherto in that respect, the degree of measuring accuracy is limited by virtue of the fact that the display of the measured thickness of the layer in question appears in the eyepiece in the form of a dark measuring strip which covers over a certain area on the scale.

SUMMARY OF THE INVENTION

An object of the present invention is to provide a method and apparatus for investigating physical properties of a surface of a testpiece such as a layer thereon, which provides an enhanced level of measuring accuracy.

Another object of the present invention is to provide a comparison ellipsometer which permits physical surface properties to be ascertained readily but with a high degree of accuracy.

These and other objects are achieved by means of an ellipsometric apparatus for studying the physical properties of the surface of a testpiece or a layer or film on a surface, comprising a polarising means for diverting polarised radiation on to two surfaces, one of which is a reference surface with a reflection characteristic or property which varies in one direction while the other of those surfaces is a surface of a testpiece to be studied, the surfaces being so arranged that the radiation is reflected thereat with the same angles of incidence and planes of incidence which are perpendicular to each other, or with a direction of polarisation which is turned through 90°, between the two surfaces. The apparatus further comprises an analyser which extinguishes the radiation reflected by the second or downstream surface, in respect of the component thereof which is in the same state of polarisation as upstream of the first reflection of the radiation. The reference surface has first and second surface portions having different reflection characteristics which are substantially symmetrical with respect to the testpiece reflection characteristics which are to be determined or which are selected, at which the radiation is simultaneously reflected.

In an advantageous embodiment of the apparatus, the reflection characteristics of the first and second surface portions of the reference surface are such that an analyser disposed downstream of the testpiece forms surface regions or grey zones with the same pattern of intensity, around the extinction strips. In another advantageous feature of the invention, the above-mentioned analyser forms two extinction strips whose mutually overlapping edge regions or grey zones, in their overlap region, form a measurement line in respect of the reflection characteristics of the testpiece. The reflection factor of the surface of the testpiece is between the two values of the two surface portions of the reference surface, while the reflection characteristics of the surface of the testpiece are approximately mean values in respect of those of the two surface portions of the reference surface. The difference between the reflection characteristics of the two surface portions of the reference surface advantageously remains the same in the direction of variation while the change in the reflection characteristics of the two surface portions is such as to be linear. The two surface portions of the reference surface may advantageously have surface layers which are of different thicknesses and which extend in mutually parallel relationship while in an advantageous feature the reflection characteristics, along the two surface portions in the same direction, have a change which is the same in percentage terms, for both surface portions. The two surface portions of the reference surface may be formed by two halves of the reference surface, or they may be formed by a strip-like grid, with the respectively adjoining strip portions of the grid pattern alternately having the different reflection characteristics referred to above. The surface portions of the reference surface may also be formed by a grid configuration made up of square or rectangular portions, or triangular portions. The two surface portions of the reference surface are advantageously of substantially the same areas. The apparatus may also be such that the testpiece to be investigated and studied is arranged to be movable while, in order to compensate for an asymmetry in respect of the intensity of distribution of radiation around the radiation extinction strips, the read-off scale may be suitably displaced by appropriate means.

In another advantageous feature, the spacings of the scale portions from each other are of suitably different magnitudes in order to compensate for asymmetry of distribution of intensity of the radiation as referred to above.

Another advantageous feature provides that, where the surface portions of the reference surface have layers thereon of wedge-shaped or tapering cross-sectional configuration, of different thicknesses, the smallest thickness of the thicker of the layers on the one surface portion is at least substantially equal to the greatest thickness of the thinner layer on the other surface portion. The reference surface may comprise a plurality of sets of the first and second surface portions, each set being of different reflection characteristics from each other set, to permit the apparatus to be used for investigating a range of testpieces by using the appropriate set of surface portions on the reference surface in the apparatus. It would likewise be possible for the reference surface to comprise first and second sets of the first and second reference surface portions, with the reflection characteristics of one set being different from those of the other set, to permit the apparatus to deal with two main ranges of testpieces.

With a construction of the apparatus in accordance with the invention, for example when measuring the thicknesses of layers or films on the surfaces of testpieces, it is possible to use a reference surface which has layers thereon of shallow wedge-shaped or tapering cross-sectional configuration, for example in a range of from 5 nm to 500 nm. Such reference layer thicknesses, in conventional manner, would form a relatively wide extinction or measuring strip in the eyepiece of the ellipsometer, so that the degree of measuring accuracy that can be attained cannot be increased. In accordance with the apparatus of the present invention, that difficulty is avoided in that, by making use of the symmetry of distribution of intensity on both sides of the extinction strips, the reference surface is divided into two surface portions which have different reflection characteristics or properties, as indicated above, those characteristics varying in linear fashion in a given direction. As indicated, that variation is substantially the same in percentage terms for both surface portions of the reference surface, and is in the same direction. When the apparatus is to be used for measuring the thickness of a layer, it is possible for that purpose to employ wedge-shaped or tapered reference layers for the two surface portions of the reference surface, those layers or surface portions extending in parallel relationship with each other. As will be more clearly apparent hereinafter, the reflection characteristics of the first and second surface portions are such that they are in substantially symmetrical relationship to the reflection characteristic of the testpiece. The tapering configuration of the layer thicknesses on the two surface portions of the reference surface makes it possible to cover a given range with which it is then possible to measure certain reflection characteristics, for example parameters which influence the reflection phenomenon at surfaces, such as the thickness of a layer on a surface of a testpiece.

Thus, the analyser which is disposed downstream of the testpiece to be studied, as will be described in greater detail hereinafter, produces two extinction strips whose mutually overlapping edge regions or grey zones, in their region of overlap, form a sharp measuring line which can be clearly perceived in the eyepiece, in respect of the reflection characteristic of the testpiece and more particularly for example the thickness of a layer on the surface thereof.

Further objects, features and advantages of the present invention will be apparent from the following description of a preferred embodiment of the apparatus.

BRIEF DESCRIPTION OF THE DRAWINGS

FIG. 1 is a diagrammatic view of the variation in intensity of a measuring strip which appears in the eyepiece of a comparison ellipsometer, FIG. 2 is a diagrammatic view in cross-section through an embodiment of a reference surface, FIG. 3 shows a cross-sectional configuration of another embodiment of the reference surface, FIG. 4 shows a plan view of the reference surface shown in FIG. 2, FIG. 5 shows a plane view of the reference surface shown in FIG. 3, FIG. 6 is a plan view of a further embodiment of the reference surface, FIG. 7 is yet another embodiment of the reference surface.

DESCRIPTION OF THE PREFERRED EMBODIMENT

Figure 8:
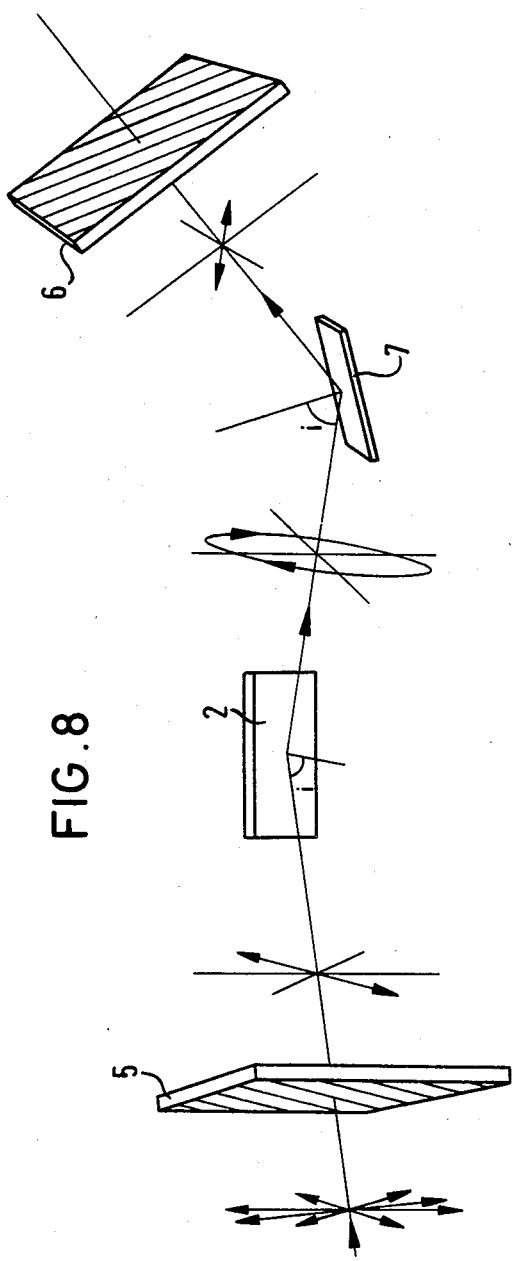
FIG. 8 is a diagrammatic view of an embodiment of the ellipsometer.

Reference will first be made to FIG. 8 which in highly diagrammatic form shows an ellipsometer apparatus. In the arrangement shown in FIG. 8, an incident parallel radiation is linearly polarised, at $-45°$, by means of a polariser 5. The polarised radiation downstream of the polariser 5 impinges on a reference surface 2 by means of which it is reflected. The light reflected from the reference surface 2 is subjected to elliptical polarisation, depending on the nature of the reference surface. The reference surface has certain characteristics which affect the reflection phenomenon and may have the surface configurations shown in FIGS. 2 to 6, as will be described in greater detail hereinafter.

Downstream of the reference surface 2 is a testpiece surface as indicated at 7 which is so arranged that the light impinges on the testpiece surface 7 with the same angle of incidence, as indicated by i, as the angle of incidence on the reference surface 2. In the embodiment illustrated herein, the reference surface 2 and the testpiece surface 7 are so arranged that their planes of incidence are normal to each other, thereby ensuring that the direction of polarisation of the radiation or light is turned through 90°, that is to say, the light leaving the testpiece surface 7 is linearly polarised at $+45°$.

It will be appreciated that, instead of the arrangement of the reference surface 2 and the testpiece surface 7 as illustrated in FIG. 8, it is also possible to use for example an optical component such as a prism which turns the direction of polarisation of the light through 90° between the surfaces 2 and 7.

Finally, disposed downstream of the testpiece surface 7 is an analyser as indicated at 6 in FIG. 8. The polariser 5 and the analyser 6 remain fixed in their set positions and their directions of polarisation are at a right angle to each other.

When the ellipsometric apparatus illustrated is used for measuring the thickness of a layer at the testpiece surface as indicated at 7, the reference surface 2 has first and second substantially identical surface portions 3 and 4, as shown in greater detail in FIGS. 2 to 7. The surface portions 3 and 4 have different reflection properties or characteristics by virtue of the fact that films or layers which are of a wedge-like or tapering configuration are provided on a base body 1, as can be clearly seen for example from FIGS. 2 and 4. As can be seen more particularly from the embodiment shown in FIGS. 2 and 4, the surface (not referenced) of the body 1 is covered over one half of the surface (surface portion 4) by a layer or film which is of a shallow wedge-like or tapering configuration in regard to its thickness, as can be seen most clearly from FIG. 2. Likewise, the other half of the surface of the body 1, constituting the surface portion 3, is covered by a film or layer which is also of a wedge-like or tapering configuration. The configurations of the two layers are in parallel relationship to each other, although it will be appreciated by looking at FIG. 2 that the layer on the surface portion 3 is thicker than that on the surface portion 4. In the illustrated embodiment, the difference in thickness between the layers on the surface portions 3 and 4 is 5 nm along the entire layer configuration. In the case of the surface portion 4 shown in FIG. 2, the thickness of the layer in the illustrated embodiment begins at 15 nm and finishes at 20 nm. On the other hand, in respect of the surface portion 3, the thickness of the layer begins at 20 nm and finishes at 25 nm.

The two layers on the surface portions 3 and 4 shown in FIGS. 2 and 4 comprise a material having the same refractive index, for example $SiO_2$. When a reference surface 2 which is of the above-defined nature and configuration is introduced into the ellipsometric apparatus, together with a testpiece surface to be investigated or studied, it is possible precisely to ascertain the thicknesses of layers on the testpiece surface if such thicknesses lie within a range of from 17.5 nm to 22.5 nm. For that range of thicknesses of layers on the testpiece surface, the apparatus ensures that, by virtue of the two surface portions 3 and 4 constituting the reference surface 2, two extinction strips are formed by the analyser 6, the edge portions or grey zones of which overlap each other and, in the region of overlap, form a relatively sharp measuring line which on the display scale shows the precise thickness of the layer or film on the testpiece surface 7.

In the above-described embodiment of FIGS. 2 and 4, and likewise in regard to the other embodiments illustrated by way of example in FIGS. 3 and 5 to 7, the layers on the surface portions 3 and 4 of the reference surface are of such a dimension that the smallest thickness of the thicker layer, on the surface portion 3 in the case of the embodiment shown in FIGS. 2 and 4, is equal to the greatest thickness of the thinner layer which is on the surface portion 4. It will be seen with reference to FIG. 2 that for example the smallest thickness of the layer on the surface portion 3, which is 20 nm, is equal to the greatest thickness of the thinner layer on the surface portion 4, being also therefore 20 nm. In the embodiment illustrated in FIGS. 2 and 4, the difference between the two layer configurations which extend in mutually parallel relationship on the respective surface portions 3 and 4 is 5 nm. That means that, with the illustrated embodiment, it is possible precisely to measure the thicknesses of layers on the testpiece surface, which are in a range of from 17.5 nm to 22.5 nm, as indicated above.

At this point reference will be made to FIG. 1 which shows that the extinction line has a distribution in respect of intensity which is in the form of a parabola and which is of substantially symmetrical configuration at both sides of the blackening maximum as indicated at $d_M$ which represents the ideal measurement value in respect of the layer thickness to be measured. When using the above-described apparatus, use is made of the effect which occurs when measuring thin layers or films, that the reference layer thicknesses on the reference surface 2 are on the two sides of the above-indicated maximum $d_M$, and have a constant spacing of $\Delta d$ over their entire range. In the illustrated embodiment $\Delta d$ is 5 nm, as indicated above.

As has already been mentioned hereinbefore, in the embodiment shown in FIGS. 2 and 4 the reference surface 2 is formed by two halves 3 and 4, with layers of a generally shallow tapering configuration which are disposed in mutually parallel relationship, with a difference of 5 nm between the thicknesses of the two layers.

Reference will now be made to FIGS. 3 and 5 showing a reference surface having surface portions thereon formed by a strip grid, as can be clearly seen from FIG. 5. It will be seen therefore that the surface on the tops of the raised portions of the grid configuration, that can be clearly seen in cross-section from FIG. 3, constitute one surface portion while the floors of the depressions between the raised portions constitute the other surface portion 4.

In the case of the construction shown in FIG. 6, the surface portions of the reference surface are defined by a grid configuration made up of square or rectangular portions while in the construction shown in FIG. 7 the grid configuration is made up of triangular portions. It will be appreciated that it is also possible to use other grid forms and configurations for the two surface portions 3 and 4, on which the various tapering layer thicknesses of the reference surface are disposed.

The apparatus as described hereinbefore preferably employs monochromatic light because that then gives a monochrome distribution of intensity of the two measuring strips produced, which in their overlap region form a measuring line with sharp contours, as indicated above.

By virtue of the fact that the testpiece 7 is so disposed in the apparatus that it can be moved, it is possible to detect local raised portions on the testpiece surface. Such raised portions may be formed for example in biomolecular reactions, for example in antigen-antibody reactions.

Minor asymmetry of the distribution of intensity at the extinction strips can be compensated for by suitable displacement of the scale, which is related to the tapering layer thickness configurations in the surface portions 3 and 4 of the reference surface 2.

The degree of measuring accuracy that the invention can be found to achieve is of the order of magnitude of 0.1 nm.

In the illustrated embodiments, as can be seen for example from FIGS. 2 and 3, the layer configurations at the surface portions 3 and 4 of the reference surface 2 are of a shallow wedge-like or tapered configuration. It should be observed however that it is also possible for the layer configuration in each surface portion 3 and 4 not to be of a straight-line nature but to be of a curved form, although in that case the two curved configurations on the surface portions 3 and 4 are to be in parallel relationship to each other, that is to say, the difference in thickness between the two layers in the two surface portions 3 and 4 always remains constant over the entire reference surface 2.

It is also possible for the reference surface 2 to comprise a multiple arrangement of the two surface portions 3 and 4, that is to say, the surface 2 may comprise two or more sets or pairs of surface portions 3 and 4 which are of the above-indicated nature. It is then possible to measure or detect, on the testpiece, a correspondingly large number of surface layers with respectively different reflection characteristics, such as and more particularly different layer thicknesses thereon.

It will be appreciated that the foregoing description is given solely by way of example of the apparatus according to the invention and that various modifications and alterations may be made in the described apparatus and structures without thereby departing from the scope of the invention as defined by the appended claims.

What is claimed is:

1. Apparatus for studying surface properties of a testpiece surface by means of electromagnetic radiation to obtain a direct point-to-point comparison between the testpiece surface and a reference surface having known properties, said apparatus comprising:
   radiation source means for generating radiation along a radiation beam path toward a testpiece,
   polarizing means disposed in the radiation beam path upstream of the testpiece for receiving and polarizing said radiation to produce a polarized radiation beam,
   said testpiece having a testpiece surface for receiving and reflecting said polarized radiation beam, and
   analyzing means disposed in the radiation beam path downstream of the testpiece for extinguishing polarized radiation in said polarized radiation beam reflected by the testpiece,
   reference means having a reference surface with reflection characteristics varying in one direction, disposed between the polarizing means and the analyzing means, for receiving and reflecting said polarized radiation beam thereby providing further polarization;
   wherein the angles of incidence of the radiation at said reference surface and said testpiece surface are at least substantially identical, and wherein the polarized radiation beam reflected at one of said reference surface and said testpiece surface has a polarization direction which, being parallel to the plane of incidence at said one surface, is perpendicular to the plane of incidence at the other of said reference surface and said testpiece surface;
   wherein said reference means enables said direct point-to-point comparison between the reference surface and the testpiece surface to be made while at the same time providing phase-shift compensation, by means of said further polarizing; and
   said reference means having two surface portions at the reference surface with different reflection characteristics on their entire surface ranges, at which the radiation is simultaneously reflected, and the two different reflection characteristics of said two surface portions of the reference surface being in substantially symmetrical relationship with respect to those of the testpiece surface to be investigated.

2. Apparatus as set forth in claim 1 wherein the reflection characteristics of said surface portions are such that the analyzing means forms zones of the same pattern of intensity around extinction strips formed in the analyzing means due to a similarity of surface properties of said reference surface and said testpiece surface.

3. Apparatus as set forth in claim 1 wherein said analyzing means forms two extinction strips having mutually overlapping edge regions which in their overlap region form a measurement line in respect of the reflection characteristics of the testpiece.

4. Apparatus as set forth in claim 1 wherein the reflection characteristic value of said testpiece surface is between said different reflection characteristics of said two surface portions of said reference surface.

5. Apparatus as set forth in claim 1 wherein the reflection characteristics of said testpiece are approximately mean values of said different reflection characteriscs of said two surface portions of said reference surface.

6. Apparatus as set forth in claim 1 wherein the difference between the reflection characteristics of said two surface portions remains the same in the direction of variation thereof.

7. Apparatus as set forth in claim 1 wherein the change in the reflection characteristics of said two surface portions is linear.

8. Apparatus as set forth in claim 1 wherein said two surface portions have surface layers of different thicknesses extending in mutually parallel relationship.

9. Apparatus as set forth in claim 1 wherein said two reflection characteristics of said surface portions vary therealong in the same direction by the same amount in percentage terms.

10. Apparatus as set forth in claim 1 wherein said two surface portions are formed by first and second halves of said reference surface.

11. Apparatus as set forth in claim 1 wherein said two surface portions are formed by a strip-like grid configuration, with the alternate strip portions thereof having the respectively different reflection characteristics.

12. Apparatus as set forth in claim 1 wherein said two surface portions are formed by a grid of rectangular portions.

13. Apparatus as set forth in claim 1 wherein said two surface portions are formed by a grid of square portions.

14. Apparatus as set forth in claim 1 wherein said two surface portions are formed by a grid of triangular portions.

15. Apparatus as set forth in claim 1 wherein said surface portions of said two reference surface are of at least substantially equal areas.

16. Apparatus as set forth in claim 1 including means for moving same testpiece.

17. Apparatus as set forth in claim 1 and further including means for displacing a read-off scale for compensation for asymmetry in respect of the distribution of intensity of radiation around radiation extinction strips formed by said analyzing means.

18. Apparatus as set forth in claim 1 wherein said analyzing means includes spaced scale portions having spacings from each other that are of different magnitudes to compensate for asymmetry of distribution of intensity of the radiation around radiation extinction strips formed by said analyzing means.

19. Apparatus as set forth in claim 1 wherein each said surface portion comprises a layer of tapering configuration, the thickness of the layers forming the respective two surface portions being different from each other and the smallest thickness of the thicker of said layers being at least substantially equal to the greatest thickness of the thinner of said layers.

20. Apparatus as set forth in claim 1 wherein said two surface portions comprise a plurality of sets of said first and second surface portions.

21. Apparatus as set forth in claim 20 including a double set of said fist and second surface portions.

22. An ellipsometric method of investigation physical properties of a testpiece surface comprising: subjecting a radiation to polarization; directing said polarized radiation on to a reference surface with reflection characteristics varying in one direction and comprising first and second surface portions having different reflection characteristics on their entire surface ranges, said radiation being simultaneously reflected at said first and second surface portions, and then directed on to a said testpiece surface, said different reflection characteristics of said first and second surface portions of said reference surface being in substantially symmetrical relationship with respect to those of the testpiece surface to be investigated, said radiation being reflected with at least substantially the same angles of incidence and with polarization which is rotated through 90° betwen said reference and testpiece surfaces; and extinguishing the radiation reflected by a downstream surface, in respect of a component thereof which is in the same state of polarization as upstream of the first reflection of the radiation.

* * * * *